United States Patent [19]

Pereira Da Silva et al.

[11] Patent Number: 5,153,129
[45] Date of Patent: Oct. 6, 1992

[54] MEMBRANE PROTEIN HAVING PROTEOLYTIC ACTIVITY OBTAINABLE FROM PLASMODIUM FALCIPARUM BLOOD SCHIZONTS AND MEROZOITES

[75] Inventors: Luiz Pereira Da Silva; Catherine Breton, both of Paris, France

[73] Assignee: Institut Pasteur, Paris, France

[21] Appl. No.: 198,211

[22] Filed: May 25, 1988

Related U.S. Application Data

[63] Continuation-in-part of Ser. No. 376,926, Jul. 10, 1989, Pat. No. 5,032,397, which is a continuation of Ser. No. 45,220, Apr. 29, 1987, abandoned, which is a continuation of Ser. No. 644,727, Aug. 23, 1984, abandoned.

[30] Foreign Application Priority Data

Dec. 27, 1982 [FR] France ................. 82 21817
Dec. 27, 1982 [FR] France ................. 82 21818
Jul. 28, 1983 [FR] France ................. 83 12496
Dec. 21, 1983 [FR] France ................. 83 20510

[51] Int. Cl.⁵ .......................................... C12N 9/50
[52] U.S. Cl. ................... 435/219; 530/413; 530/820; 530/822
[58] Field of Search ........................................ 435/219

[56] References Cited

U.S. PATENT DOCUMENTS 5,032,397  7/1991  Dubois et al. .................. 424/88

OTHER PUBLICATIONS

Schrevel et al.-Chem. Abst., vol. 102 (1985) p. 74,557h.
Vander et al.-Chem. Abst., vol. 104 (1986) p. 211,149y.
Perrin et al.-Immunological Reviews, vol. 61 (1982) pp. 245 to 269.

*Primary Examiner*—Sam Rosen
*Attorney, Agent, or Firm*—Burns, Doane, Swecker & Mathis

[57] ABSTRACT

An immunogenic composition for use as a vaccine against malaria. It comprises an enzymatically active protease with a molecular weight of 76.000 daltons, characterized by its capacity to react with protective antibodies originating from monkeys resistant to human malaria parasites, particularly to *Plasmodium falciparum*.

15 Claims, No Drawings

MEMBRANE PROTEIN HAVING PROTEOLYTIC ACTIVITY OBTAINABLE FROM PLASMODIUM FALCIPARUM BLOOD SCHIZONTS AND MEROZOITES

This application is a continuation-in-part of Ser. No. 07/376,926, filed Jul. 10, 1989 now U.S. Pat. No. 5,032,397 which was a continuation of Ser. No. 07/045,220 filed Apr. 29, 1987 now abandoned, which was a continuation of Ser. No. 06/644,727 filed Aug. 23, 1984, now abandoned.

Further investigation in the *Plasmodium falciparum* membrane proteins showed that they comprised a polypeptide having a molecular weight of 76,000 daltons (or 76 Kd polypeptide) which can be released in the form of an enzymatically active protease from the membranes of intact merozoites or isolated blood-schizont membranes, when the latter are treated with a phospholipase, such as the phosphatidylinositol-specific phospholipase, C (PI-PLC), particularly a PI-PLC of *Staphylococcus aureus*. It can also be released from the parasites cells in the form of a water soluble enzyme by osmotic shock.

This PI-PLC induced 76 Kd protease is a water soluble enzymatically active protease, more particularly a serine-protease whose activity is inhibited by PMSF (phenylmethyl sulfonyl fluoride), chymostatin, leupeptin, yet it is not inhibited by pepstatin and EDTA (ethylenediamine tetracetate). It is also recognized by monoclonal antibodies which recognize inactive 76 Kd polypeptide, e.g. monoclonal antibody 31c13 disclosed in PERRIN L., DAYAL R. ; Immunological review, 61 : 245-270 (1982).

The invention relates to immunogenic compositions containing the above-mentioned enzymatically active 76 Kd protease, extracted from malarial parasites, said protease being also characterized by its capacity to react with protective antibodies originating from monkeys resistant to human parasites of malaria and particularly to species of human *Plasmodium falciparum*.

Particularly, the invention relates to immunogenic compositions containing the enzymatically active 76 Kd protease, which induces particularly in monkey, and more particularly Saimiri Sciureus monkey, active antibodies against malaria parasites, more particularly *Plasmodium falciparum* or parasites which present the same essential biological characteristics.

which is recognized by sera or other immunoglobulin compositions originating from animals, particularly Samiri Sciureus monkeys, resistant to parasites, these sera or other compositions containing the corresponding immunoglobulins being capable, by in vivo passive transfer to animals sensitive to the parasite, to protect them against said parasite.

More particularly, the 76 KD protease according to the invention is characterized by the fact that it is recognized by protective antibodies which are contained in a protective serum obtained from immunized Saimiri Sciureus monkey as a result of previous infection by FUPC I-212 *P. falciparum* strain, said serum having been collected within 10 to 90 days from the end of the acute infection.

The invention also relates to a process for obtaining such immunogenic compositions. This process comprises treating a preparation which has been obtained from a malarial infectious parasite, particularly of the *plasmodium* type, such a *Plasmodium falciparum*, particularly at the merozoite or blood schizont stage of the parasite, with a phospholipase, such as the *Staphylococcus aureus* PI-PLC, or *Trypanosoma brucei* PI-PLC, or alike, liable to induce the release of the 76 Kd protease in the soluble fraction, separating the soluble fraction from the membrane pellet, and recovering the 76 kd protease.

The recovery of the 76 kd protease can be obtained by an appropriate method, such as gel filtration, electrophoresis or alike, and particularly by contacting the solution, resulting from the treatment of the parasite with the phospholipase, with antibodies recognizing said protease, which antibodies have been previously fixed to a non-soluble support, removing the non fixed proteins, such as by washing, dissociating the complex formed between the fixed antibodies and the 76 Kd protease, and recovering said 76 Kd protease.

For instance, the above-mentioned antibodies consist of protective antibodies originating from monkey, or monoclonal antibodies such as the above-cited monoclonal antibody 31c13.

Additional characteristics of the invention will appear again in the description which follows of examples of production of the enzymatically active 76 Kd protease and of the biological properties thereof.

1) The FUP strain of *P. falciprum* (GYSIN et al, *J. Parasitol*, 66, 1003–1009 (1980)) is cultivated as described (BRAUN-BRETON et al, *Molec. Biochem. Parasitol*, 20, 33–43 (1986)). Synchronization is performed by incubation of the cells in 2 volumes of 0.3M alanine, 10 mM Hepes for 3 minutes at 37° C. Schizonts are purified on Percoll-Sorbitol gradients as described (ALEY et al, *J. Exp. Med.*, 160, 1585-1590 (1984)). $^{35}$S methionine labeling and cell fractionation were previously described (BRAUN-BRETON et al, *Molec. Biochem. Parasitol*, 20, 33–43 (1986)). The membrane fraction is resuspended in phosphate-buffered saline (PBS) and is incubated for 1 hour at 37° C., with 1 to 5 $\mu$g ml$^{-1}$ *S. aureus* PI-PLC. For immunoprecipitation, the membrane suspension is diluted in 1 volume of 20 mM Tris pH 7,5-20 mM EDTA -1 M Na Cl - 2% Triton X100, incubated for 30 minutes at room temperature and centrifuged 5 mn at 12000 rpm. The 31 c13 immunoglobulins were purified on Affigel-protein A -MAPS II (Biorad) under these conditions the IgG were depleted of the proteases present in the ascitic fluid. Purified IgG are used for immunoprecipitation as described ((BRAUN-BRETON et al, *Molec. Biochem. Parasitol*, 20, 33–43 (1986)) with the following modifications : incubation with antigen for 1 hour at room temperature in the absence of protease inhibitors. For the last wash each sample is divided into 2 equal volumes in such a way that half of the immunocomplexes are resuspended in Laemli sample buffer for polyacrylamide gel electrophoresis (SDS-PAGE) (LAEMLI et al, *Nature*, 277, 680-682 (1970)) and half resuspended in solution P (2,5% SDS, 2% sucrose, 0,1% bromophenol blue) for analysis of proteases. Electrophoretic analysis of proteases in gels containing SDS and 0,1% gelatin was previously described (HEUSSEN et al, *Anal. Biochem.*, 102, 196 (1980)).

The specific monoclonal antibody 31c13 immunoprecipitates an enzymatically active 76 Kd protease from PI-PLC treated membranes and an inactive 76 Kd polypeptide from detergent treated membranes, e.g. SDS treated membranes. Detergent extraction of membrane proteins does not solubilize an enzymatically active 76 Kd protease. Detergent does not irreversely inhibit the protease activity since the PI-PLC induced activity is resistant to identical detergent conditions, and induction of the protease activity by PI-PLC can be performed on detergent extracted membrane proteins.

2) Inhibition of protease activity by protease inhibitors

| inhibitors | PMSF 10 mM | EDTA 10 mM | Pepstatin 50 μg. ml$^{-1}$ | Leupeptin 5/50 μg. ml$^{-1}$ | Chymostatin 50 μg. ml$^{-1}$ |
|---|---|---|---|---|---|
| 76 Kd protease | − | ++ | ++ | +−/− | − |

Schizont membranes were treated with 5 μg. ml$^{-1}$ S. aureus PI-PLC, resuspended in solution P. and analyzed for protease activity as above-described. Protease inhibitors were added in the O. 1M Glycin byffer in which the gels were incubated after electrophoresis.
− no detectable protease activity.
+− faint protease activity.
+ detectable activity but lower than control (without inhibitor).
++ protease activity comparable to the control.

We claim:

1. Immunogenic composition containing a purified enzymatically active protease, extracted from malarial parasites, said protease having molecular weight of about 76,000 daltons wherein said protease is a serine protease inhibited by PMSF, chymostatin and leupeptin, but that is not inhibited by pepstatin and EDTA, and wherein said protease reacts with protective antibodies originating from monkeys resistant to human parasites of malaria and particularly to species of human *Plasmodium falciparum*.

2. A composition according to claim 1 containing said enzymatically active 76 kD protease, obtained from *P. falciparum*, which induces in monkey active antibodies against malaria parasites, and which is recognized by sera or other immunoglobulin compositions originating from animals, resistant to parasites, these sera or other compositions containing the corresponding immunoglobulins being capable, by in vivo passive transfer to animals sensitive to the parasite, to protect them against said parasite.

3. A composition according to claim 1, wherein the enzymatically active 76 Kd protease is recognized by protective antibodies contained in a protective serum obtained from immunized Saimiri Sciureus monkey as a result of previous infection by FUPC I-212 *P. falciparum* strain, said serum having been collected within 10 to 90 days from the end of acute infection.

4. Process for preparing the immunogenic composition of claim 1, comprising the steps of treating a preparation obtained from a malarial infectious parasite, with a phospholipase, separating the soluble fraction from the membrane pellet, and recovering the 76 kD protease.

5. The process of claim 4, wherein the parasite is in the merozoite or blood schizont state.

6. The process according to claim 4, wherein the 76 kD protease is recovered by gel filtration, or electrophoresis.

7. The process of claim 4, comprising contacting the solution, resulting from the treatment of the parasite with the phospholipase, with antibodies recognizing said protease, which antibodies have been previously fixed to a non-soluble support, separating the non fixed antibodies, dissociating the complex formed between the fixed antibodies and said protease, and recovering the 76 Kd protease.

8. The process of claim 7, wherein the fixed antibodies are monoclonal antibodies formed previously against the 76 Kd protease.

9. A composition according the claim 2, wherein the monkey is Saimiri Sciureus.

10. A composition according the claim 2, wherein the malaria parasite is *Plasmodium falciparum*.

11. A composition according the claim 2, wherein the animal is Saimiri Sciureus.

12. A process for preparing the immunogenic composition according to claim 4, wherein the malarial infectious parasite is Plasmodium.

13. A process for preparing the immunogenic composition according to claim 4, wherein the malarial infectious parasite is *Plasmodium falciparum*.

14. A process for preparing the immunogenic composition according to claim 4, wherein the phospholipase is *Staphylococcus aureus* PI-PLC.

15. A process for preparing the immunogenic composition according to claim 4, wherein the phospholipase is *Trypanosoma brucei* PI-PLC.

* * * * *